United States Patent [19]
Yerkovich

[11] Patent Number: 5,983,137
[45] Date of Patent: Nov. 9, 1999

[54] METHOD AND SYSTEM FOR MONITORING THE CONDITION OF A BATTERY PACK IN A DEFIBRILLATOR

[75] Inventor: Daniel Yerkovich, Snohomish, Wash.

[73] Assignee: Physio-Control Manufacturing Corporation, Redmond, Wash.

[21] Appl. No.: 08/914,865

[22] Filed: Aug. 19, 1997

[51] Int. Cl.[6] .................................................. A61N 1/39
[52] U.S. Cl. ........................................................ 607/5
[58] Field of Search ................................. 607/5, 27, 29

[56] References Cited

U.S. PATENT DOCUMENTS

| | | |
|---|---|---|
| 4,207,514 | 6/1980 | Klein . |
| 4,259,639 | 3/1981 | Renirie . |
| 4,525,055 | 6/1985 | Yokoo . |
| 4,590,941 | 5/1986 | Saulson et al. ............................ 607/29 |
| 4,590,943 | 5/1986 | Paull et al. . |
| 4,610,254 | 9/1986 | Morgan et al. . |
| 4,693,119 | 9/1987 | Johnson . |
| 4,725,784 | 2/1988 | Peled et al. . |
| 5,065,084 | 11/1991 | Oogita . |
| 5,130,659 | 7/1992 | Sloan . |
| 5,162,741 | 11/1992 | Bates . |
| 5,250,905 | 10/1993 | Kuo et al. . |
| 5,483,165 | 1/1996 | Cameron et al. . |
| 5,773,961 | 6/1998 | Cameron et al. ............................ 607/5 |

FOREIGN PATENT DOCUMENTS

| | | |
|---|---|---|
| 0 566 386 A1 | 10/1993 | European Pat. Off. . |
| 0 712 008 A2 | 5/1996 | European Pat. Off. . |
| 2 734 061 | 11/1996 | France . |

*Primary Examiner*—William E. Kamm
*Assistant Examiner*—George R. Evanisko
*Attorney, Agent, or Firm*—Christensen, O'Connor, Johnson & Kindness, pllc

[57] ABSTRACT

A method and system for monitoring the capacity of a battery pack (6) is provided. The battery pack (6) is capable of delivering current to a load ($R_L$). The battery pack (6) includes a monitor cell (C4) and battery cells (C1, C2, and C3). The monitor cell (C4) has a predetermined initial energy level that is lower than the predetermined initial energy level of the battery cells. A monitoring system (22) including an analog-to-digital converter (10) and a microprocessor (12) is connected to the battery pack and monitors the voltage of the battery pack. When the monitoring system detects a voltage change indicating depletion of the monitor cell (C4), the monitoring system provides a signal indicative that the battery pack is nearing depletion.

16 Claims, 4 Drawing Sheets

METHOD AND SYSTEM FOR MONITORING THE CONDITION OF A BATTERY PACK IN A DEFIBRILLATOR

FIELD OF THE INVENTION

The present invention relates generally to a method and system for monitoring batteries and determining the condition of a battery pack in a defibrillator.

BACKGROUND OF THE INVENTION

Batteries are often used to power portable electronic devices. After a period of use, the batteries in a portable device will become depleted and affect the performance of the portable device. When the energy level of the batteries falls below a certain threshold, the portable device will cease to operate. At this point, the batteries must be recharged or replaced. Accordingly, in many applications it would be beneficial to monitor the remaining charge in the batteries and alert the user of a portable device before the batteries are depleted.

One environment where monitoring the remaining charge in batteries is important is in portable external cardiac defibrillators. Portable cardiac defibrillators generate and apply a high energy defibrillation pulse to the chest of a patient to cause the patient's heart to stop fibrillating and return to a normal rhythm. Sometimes the application of a single defibrillation pulse fails to restore the patient's heart to a normal rhythm. In such an event, it may be necessary to apply additional defibrillation pulses. Portable external defibrillators generally use a battery pack containing a number of cells to power the defibrillator. The battery pack allows an energy storage capacitor to be charged in order to generate a defibrillation pulse. If the battery pack becomes depleted, the patient cannot be treated.

In order to assure that an external cardiac defibrillator is always ready for use, it is therefore advantageous to monitor the remaining charge in the battery pack. Battery monitoring provides an indication of when the battery pack is nearly depleted and needs to be replaced or recharged.

Various efforts in the prior art have been devoted to monitoring the remaining energy in a battery pack. One common approach entails measuring an output voltage from the battery pack while the battery pack is connected to an electrical load. As the battery pack is discharged, the voltage will typically drop. Variations of this approach involve measuring other battery parameters, such as the impedance of the batteries in the battery pack, to detect changes that indicate that the battery pack is nearing the end of its useful life.

One disadvantage of monitoring the output voltage from the battery pack to detect a drop in voltage is that the method is unable to accurately monitor the energy level of typical nonrechargeable batteries. FIG. 1 depicts the output voltage v from a single nonrechargeable lithium battery plotted with respect to time. The output voltage from the lithium battery remains relatively constant until near the end of its life t when the output voltage drops precipitously. Because of the steep drop in voltage, it is nearly impossible to give sufficient advance warning when the battery pack is nearly depleted. By the time the battery voltage begins to drop, insufficient energy often remains in the battery pack to power the electronic device for any appreciable period. This is especially true for devices which have a high energy utilization rate such as defibrillators.

Another approach for determining the remaining charge in a battery pack is disclosed in U.S. Pat. No. 5,483,165 to Cameron et al. Cameron et al. disclose a defibrillator having a main battery consisting of a number of identical battery cells connected in series. A sense cell is connected in series to the main battery. The sense cell is identical in type and manufacture to each of the main battery cells. A current flows through the main battery and the sense cell to a load. Because all the cells are identical, the sense cell and battery cells in the main battery should in normal circumstances be depleted at the same rate. However, Cameron et al. disclose a dedicated circuit for drawing additional, incremental current from the sense cell. The value of the incremental current equals the value of the current delivered to the load scaled by an arbitrary constant. The dedicated circuit drawing the incremental current includes a variable resistance connected between the sense cell and ground potential. The variable resistance is used to vary the value of the incremental current drawn from the sense cell.

The sense cell in Cameron et al. is used to estimate the remaining charge in the main battery. Since the sense cell is discharged at a quicker rate than the main battery, the voltage drop characteristic of battery cells at the end of their useful life will first occur on the sense cell. When the voltage drop on the sense cell is detected by a controller, a signal or other warning is generated to indicate that the main battery is also nearly depleted.

While the Cameron et al. approach offers some advantages over other prior art techniques for monitoring batteries, it also presents disadvantages. The need to draw an additional current from a sense cell adds undue complexity and, it will be appreciated, problems attendant with that complexity. For example, the Cameron et al. approach requires adding a dedicated voltage monitor and a variable resistance circuit to draw the incremental current from the sense cell. The additional components and battery contacts required to draw the incremental current increase the likelihood that a component in the battery monitoring system could fail and render the battery monitoring technique ineffective.

Apart from the increased likelihood of failure, the need to provide a voltage monitor and variable resistance poses other problems. The addition of the voltage monitor and the variable resistance increases the cost of a device incorporating the battery monitoring system. The voltage monitor and the variable resistance also add weight and size to the system.

The use of additional circuitry to draw an incremental current from the sense cell also limits the interchangeability of the type of battery cell incorporated in a battery pack. For example, if lithium battery cells are used in the battery packs, a certain incremental current must be used that corresponds to the anticipated voltage curve of the lithium battery cell. If there is an improvement in battery technology or if a user desires to use a different type of battery cell, such as a rechargeable nickel cadmium battery cell, a different amount of incremental current should be drawn from the new cell to correspond to the anticipated voltage curve of the new cell. An operator of the portable electronic device must therefore somehow adjust the amount of incremental current drawn depending upon the type of battery pack that is to be used in the device. The need to perform an additional adjustment limits the ease with which the user may select a type of battery suitable for a particular application.

In addition to monitoring the remaining charge in the battery pack, it would also be advantageous to monitor the health of the individual battery cells within the battery pack in order to detect a possible cell failure. Individual cell failures decrease the energy storage capacity of the battery pack and can also detrimentally affect the performance of the battery pack during discharge of the battery pack.

As can be seen from the discussion above, there exists a need for improved methods of monitoring the condition of battery packs. The present invention is directed toward addressing this need.

SUMMARY OF THE INVENTION

In one embodiment of the present invention, a method and system for monitoring the condition of a battery pack of a defibrillator is provided. The battery pack includes a plurality of battery cells, at least one of which is designated as a monitor cell. In one embodiment, the monitor cell has an initial energy level lower than at least one of the plurality of other battery cells. The monitoring system includes an analog-to-digital converter and a microprocessor connected to the battery pack for monitoring the output voltage from the battery pack. When the monitoring system detects a voltage change or a rate of voltage change across the battery pack that is greater than a threshold value, the monitoring system alerts an operator that the battery pack is nearly depleted.

In accordance with one aspect of the invention, the capacity of the battery pack and the monitor cell is predetermined so that the defibrillator may continue to operate on the voltage provided by the remaining battery cells in the battery pack after depletion of the monitor cells.

In accordance with one aspect of the invention, the monitor cell is rated at less ampere hours than the other cells in the battery pack. Alternatively, the monitor cell is discharged to a predetermined level prior to being connected to the other cells in the battery pack.

In accordance with still other aspects of the invention, the monitoring system provides an indication of an approximate number of shocks that the defibrillator is capable of providing upon detection of the depletion of the monitor cell. In embodiments in which multiple monitor cells are used, the monitoring system detects the depletion of individual monitoring cells and provides an indication of the operating capacity of the defibrillator upon depletion of each monitor cell.

In another embodiment of the invention, a method for identifying the presence of a damaged or depleted battery cell in a rechargeable battery pack having a plurality of cells is provided. The battery pack is connected to a load to allow the battery pack to deliver current to the load. A voltage or rate of change in voltage across the battery pack is measured during application of the current to the load. The measured voltage or rate of change in voltage is compared with a threshold value to provide an indication of the presence of a depleted or damaged battery cell.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 2:
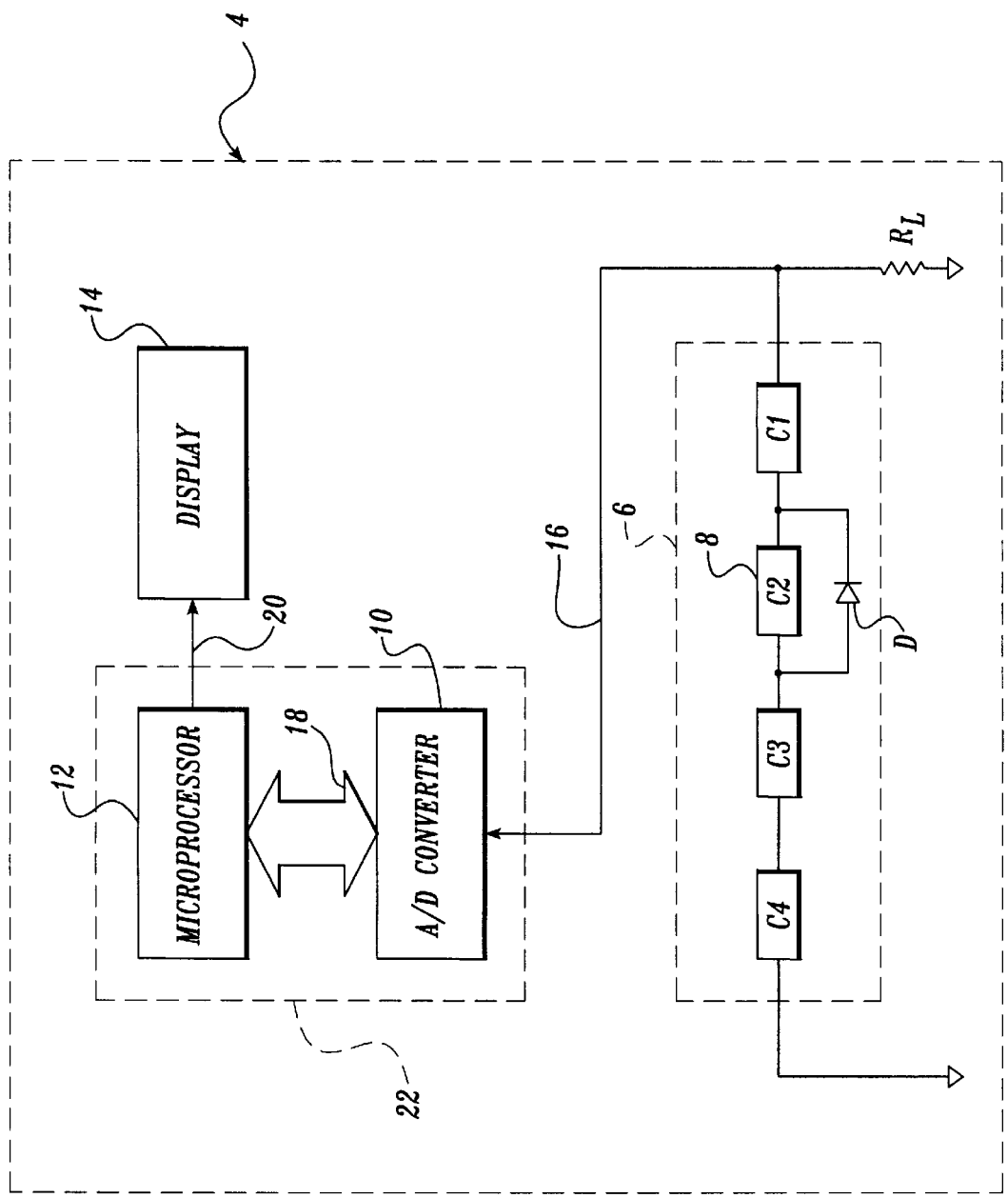
FIG. 2 is a block diagram of a system for monitoring the condition of a battery pack in accordance with the present invention.

The present invention detects the condition of a battery pack in a defibrillator or other device in which the battery pack is located. In accordance with one embodiment of the invention, the voltage of the battery pack is monitored to provide indications about the remaining charge of the battery pack and the condition of individual cells in the battery pack. FIG. 2 is a block diagram of one embodiment of the invention for monitoring the remaining charge in a battery pack 6 incorporated in a portable electronic device, such as a portable defibrillator 4. Battery pack 6 comprises a plurality of battery cells C1, C2, C3 and C4 that are coupled in series so that the output voltage of the battery pack is equal to the sum of the output voltage from each individual battery cell. While four cells are depicted in FIG. 2, it will be appreciated that any number of battery cells may be incorporated in the battery pack, depending on the output voltage required to power the electronic device containing the battery pack.

One of the battery cells C1, C2, C3, or C4 is designated a monitor cell 8. FIG. 2 depicts cell C2 as the monitor cell, however, it will be appreciated that any of the other cells in the battery pack could be used as a monitor cell. A diode D is coupled in parallel with the monitor cell so that it is forward biased if the monitor cell is depleted or fails. Diode D provides a conductive path so that when the monitor cell is depleted, the battery pack continues to produce an output current.

Preferably, each of the battery cells C1, C2, C3, and C4 have substantially the same output voltage and type of construction. The battery cells may be any type of cell, including, but not limited to, lithium cells, nickel-cadmium cells, alkaline cells and zinc-carbon cells. As discussed in additional detail below, in the preferred embodiment the battery cells C1, C3, and C4 are fully-charged cells that have approximately the same energy storage capacity and initial energy charge level. The monitor cell 8, however, is configured to have less energy stored in it initially than the energy stored in each of the battery cells C1, C3, and C4.

The negative terminal of battery pack 6 is coupled to ground, and the positive terminal of the battery pack is coupled to a load $R_L$. Load $R_L$ represents any load to which current from the battery pack 6 is delivered. For example, when the battery pack is incorporated in the defibrillator 4, load $R_L$ represents a circuit for charging an energy storage capacitor (not shown) to allow a defibrillation pulse to be applied to a patient experiencing ventricular fibrillation, or other shockable rhythm.

A monitoring system 22 is provided to monitor the output voltage from the battery pack 6 and determine when the battery pack is nearly depleted. The monitoring system 22 includes an analog-to-digital converter 10 and a microprocessor 12. The positive terminal of the battery pack 6 is connected to the analog-to-digital converter 10 by a line 16. The analog-to-digital converter 10 measures the voltage across the battery pack and converts the voltage into a digital signal. The digital signal is provided to the microprocessor 12 over a bus 18 to allow the microprocessor to monitor the voltage or rate of change in the voltage across the battery pack (hereinafter voltage change shall mean either a change in voltage or a change in the rate of change of the voltage).

In the preferred embodiment, the monitor cell has approximately the same energy storage capacity as the other battery cells. However, prior to assembly of the battery pack 6, the amount of energy in the monitor cell 8 is set so that it is less than the initial energy contained in each of the battery cells C1, C3, and C4. Two techniques may be used to ensure that the monitor cell contains less energy than the other cells. The monitor cell may be selected so that it is rated at less ampere-hours than the other battery cells when in a fully charged state. Alternatively, the monitor cell C8 may be discharged by drawing a known current from the monitor cell C8 for a predetermined period of time. For example, the discharge can be accomplished by connecting a resistor to the monitor cell C8 to draw a current from the monitor cell for a predetermined time.

After the amount of energy in the monitor cell is set, the battery pack is assembled and placed in the defibrillator. As current from the battery pack 6 is delivered to the load $R_L$, the battery cells C1, C3, C4 and the monitor cell 8 are discharged at an approximately equal rate. Because the battery cells C1, C2, C3, and C4 are connected in series and the initial energy level of the monitor cell 8 is lower, the monitor cell 8 is depleted before the battery cells C1, C3, and C4. When the monitor cell 8 is depleted, the output voltage from the monitor cell will drop as depicted in FIG. 3.

Figure 1:
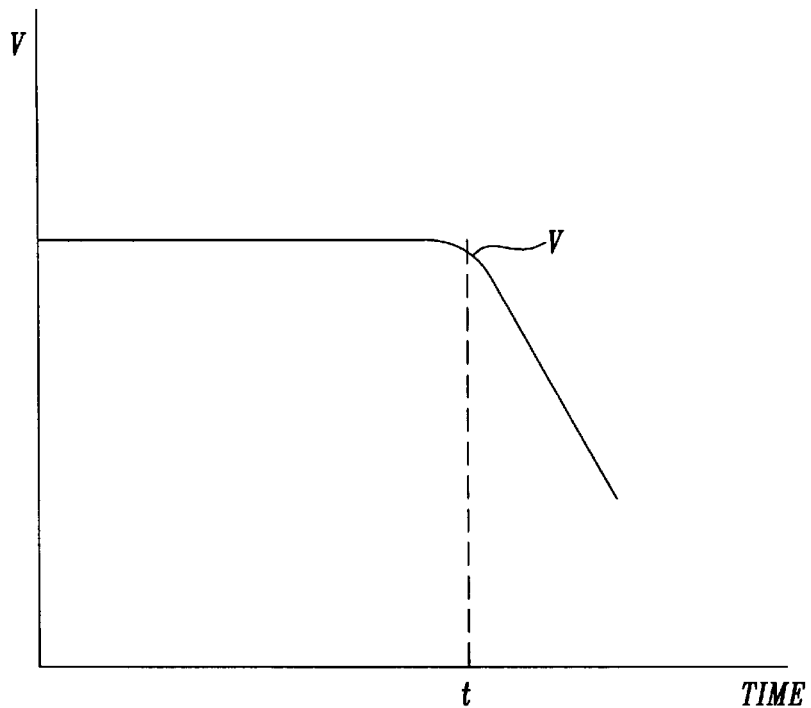
FIG. 1 is a graph depicting the output voltage from a typical non-rechargeable battery pack plotted with respect to time.
Figure 3:
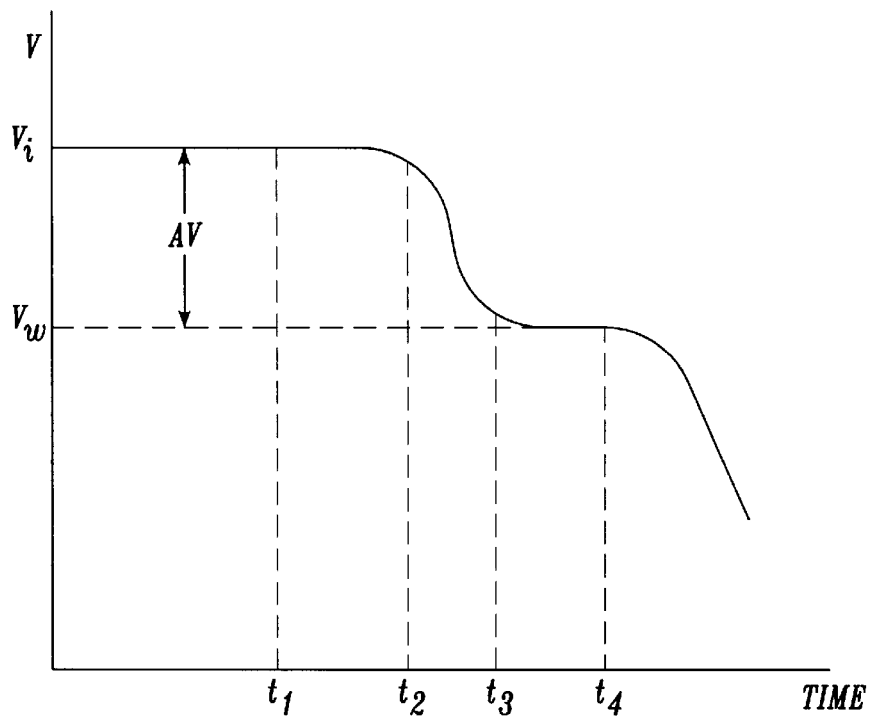
FIG. 3 is a graph depicting the output voltage of the battery pack of FIG. 2 plotted with respect to time.

FIG. 3 is a graph of the output voltage from the battery pack 6. The abscissa represents time, while the ordinate represents voltage. The initial input voltage $V_i$ from the battery pack is equal to the sum of the output voltages from all the cells in the battery pack. For most of the battery pack life, the output voltage remains at or near the initial voltage level $V_i$. At a time $t_2$, the monitor cell 8 becomes nearly depleted and the output voltage from the monitor cell drops quickly. The output voltage from the battery pack therefore drops by a corresponding amount, from the initial voltage level $V_i$ to an intermediate voltage level $V_W$ at time $t_3$. The intermediate voltage level $V_W$ is equal to the sum of the output voltages from the remaining cells C1, C3, and C4, minus the forward drop of diode D.

It will be appreciated that the monitor cell 8 may be an open circuit when depleted. Diode D bypasses the monitor cell and acts as a current bypass around the monitor cell 8 so that the battery pack will continue to provide current to the defibrillator.

The battery pack continues to provide the intermediate output voltage $V_W$ for a period of time following time $t_3$. In the preferred embodiment, the output of the battery cells and thus the intermediate output voltage $V_W$ is predetermined to be adequate to continue to power the defibrillator with little or no loss of device performance. The continued delivery of current by the battery pack 6 will ultimately cause battery cells C1, C3, and C4 to become depleted. At time $t_4$, the battery cells C1, C3, and C4 are nearly depleted and the output voltage from the battery pack drops quickly. Following time $t_4$, the output voltage from the battery pack may be insufficient to power the defibrillator.

The detection of the voltage change from the initial voltage $V_i$ to the intermediate voltage $V_W$ is used to warn an operator of the portable equipment of the remaining charge in the battery pack 6. When the microprocessor 12 detects the voltage change caused by the depletion of the monitor cell, a warning is provided to the operator on a display 14. The warning may be an audible or visual alarm. The warning indicates to the operator that the battery pack 6 will soon be completely discharged and that the battery pack should be replaced or recharged before the device fails.

As indicated above, the voltage of the battery pack remains approximately constant until the battery pack is nearly depleted. Therefore, the voltage change caused by the depletion of the monitor cell 8 is easily detected by the microprocessor. The microprocessor is preprogrammed to detect when a voltage change greater than a predetermined threshold is detected. Thus, the microprocessor detects when the monitor cell is depleted and then provides a warning to the operator to indicate that the monitor cell is depleted, and thus the battery pack 6 is nearing depletion.

In the preferred embodiment, the battery pack 6 is used within an external defibrillator. In such embodiment, the battery pack is carefully sized so that upon depletion of the monitor cell the battery pack still contains enough energy to operate the defibrillator during a predetermined range of shocks. Thus, the battery pack is sized to insure that the operator is provided an indication of the battery pack nearing depletion prior to the defibrillator's being unable to defibrillate a patient. In the preferred embodiment, the battery pack's energy level is sized to allow the defibrillator to operator for approximately a predetermined number of defibrillation shocks. Thus, the microprocessor may also provide an indication to the operator of approximately how many defibrillation shocks the defibrillator can provide prior to depletion of the battery pack. The indication of the number of shocks left within the battery pack is, of course, approximate because of variations in battery cell construction, varying discharge rates of the batteries.

The initial energy level of the monitor cell 8 is calibrated so that the approximate amount of charge remaining in battery cells C1, C3, and C4 is known when the monitor cell is depleted. The calibration is, of course, approximate because of variations in the battery cell construction, varying discharge rates because of climatic conditions to which the battery pack is exposed, and other factors.

In alternative embodiments of the invention, multiple monitor cells can be provided within the battery pack. Each monitor cell can have a predetermined initial energy level that is different from the other monitor cells. As the battery pack is discharged, each of the monitor cells having a different initial energy level will be depleted at a different time. The monitor circuit detects the depletion of each individual monitor cell and provides an indication of the remaining energy within the battery pack upon depletion of each individual monitor cell. Therefore, the microprocessor can be programmed to provide an indication of the remaining power within the battery pack based upon the measure of voltage after depletion of each individual monitor cell.

Based upon the measured voltage in the battery pack, the microprocessor can calculate roughly the energy storage capacity left in the battery pack and thus how many times the defibrillator can be operated prior to battery failure. The indication of remaining energy within the battery pack or how long the defibrillator can be operated for prior to depletion of the battery pack will be approximate due to the varying parameters associated with the charge and discharge of each of the cells within the battery pack, system inefficiencies within the defibrillator, and the energy provided in each shock, etc.

The present method and system for monitoring the remaining charge in a battery pack provides a simple, reliable technique to anticipate battery pack failure. The present invention has application in a variety of possible environments that require reliable battery power including external cardiac defibrillators. Conventional external cardiac defibrillators include many of the components required to implement the present invention in the defibrillator. In many cases, only a new battery pack including the diode D and the addition of software will need to be added to practice the invention.

In another embodiment of the present invention, a degraded or damaged battery cell within a battery pack can also be detected by monitoring the voltage change of the battery pack during discharge of the battery pack. It will be appreciated that battery cells may sometimes become damaged, causing irregularities in their ability to retain, accept, or deliver charge. Such damage to battery cells may result from a variety of circumstances. For example, a degradation in battery cell performance occurs when the seals of a cell fail and let it dry out. As another example, contamination of a battery cell can occur when the battery cell is recharged. Such contamination can undesirably generate leakage currents within the battery cell, and thereby deplete the energy stored therein. When damage to a battery cell occurs, the damaged battery cell is preferably detected and removed from further use.

Figure 4:
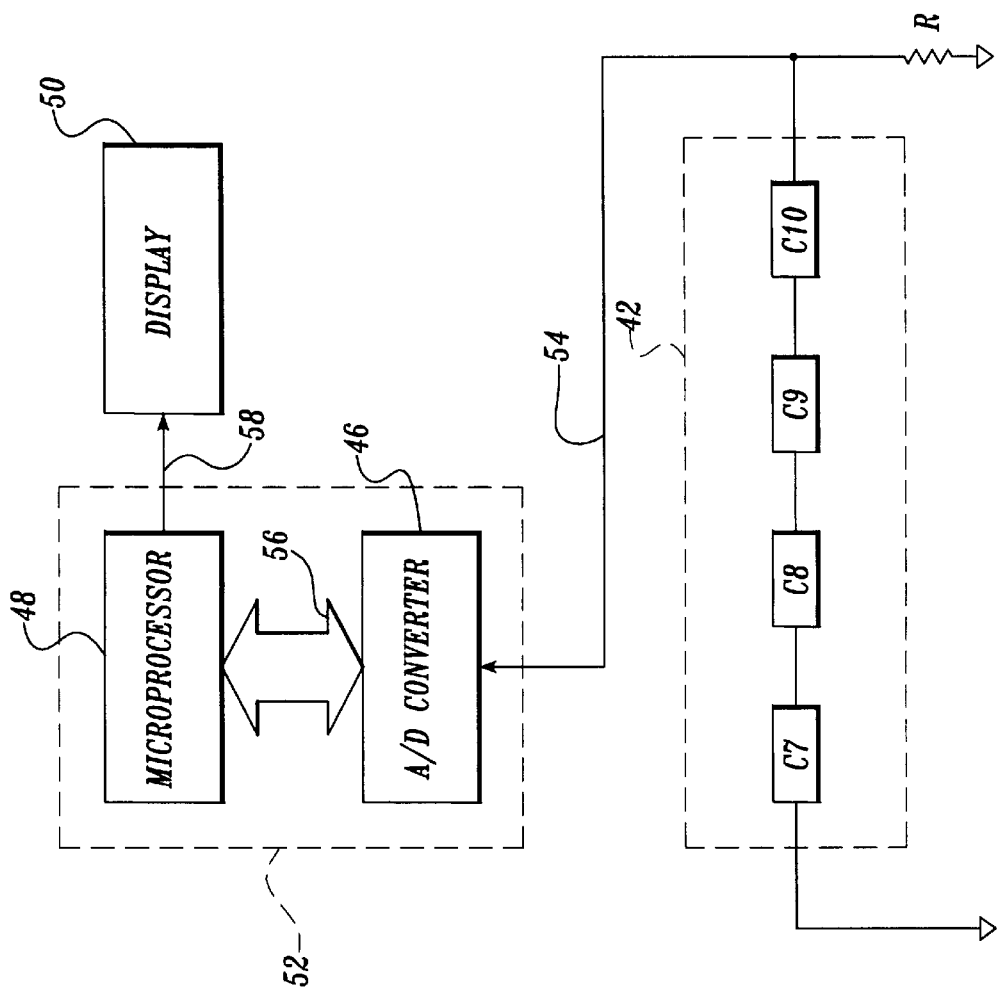
FIG. 4 is a block diagram of a system for detecting a damaged battery cell in a battery pack in accordance with an alternative embodiment of the present invention.

The present invention detects a damaged battery cell in a battery pack by monitoring the voltage change of the battery pack during discharging. FIG. 4 is a block diagram of a system for monitoring the voltage on a battery pack 42. As will be noted, the system of FIG. 4 is similar to the system of FIG. 2 without the use of the diode D. The battery pack 42 comprises a plurality of battery cells C7, C8, C9, and C10 that are connected in series. The voltage of the battery pack 42 is equal to the sum of the voltages of each battery cell. While four cells are depicted in FIG. 4, it will be appreciated that any number of battery cells may be incorporated in accordance with the present invention.

Each of the battery cells C7, C8, C9, and C10 initially have a positive voltage and are connected so that the negative terminal of one battery cell is connected to the positive terminal of an adjacent battery cell. The battery cells C7, C8, C9, and C10 are rechargeable cells that are not necessarily fully charged. The positive terminal of the battery pack 42 is connected to ground potential through a resistor R. Resistor R represents any load to which current is delivered. For example, if the battery pack 42 is used to charge an energy storage capacitor in a defibrillator, resistor R represents a circuit for charging the energy storage capacitor and delivering a defibrillation pulse to a patient experiencing ventricular fibrillation.

A preferred monitoring system 52 is provided to detect the voltage change of the battery pack 42 either during or after some current has been delivered to resistor R. The monitoring system 52 includes a microprocessor 48 and an analog-to-digital converter 46. The positive terminal of the battery pack 42 is connected to the analog-to-digital converter 46. The analog-to-digital converter 46 measures the voltages across the battery pack 42 and converts the voltage into a digital signal. The digital signal is provided to the microprocessor 48 over a bus 56. The microprocessor 48 calculates the voltage change of the battery pack 42 due to the delivery of current to resistor R. More specifically, as described in more detail below, the microprocessor 48 detects damage to a battery cell by identifying when the voltage change exceeds a predetermined threshold.

When used to monitor a charged battery pack, prior to any delivery of current, the voltage of the battery pack 42 has a maximum value which, as stated above, is the sum of the voltages of each battery cell. As described above, as the battery pack 42 delivers current to the resistor R, the voltage $V_1$ of the battery pack 42 will very gradually decrease until the battery pack nears depletion and will then drop sharply. In the event that a battery cell within the battery pack 42 becomes damaged, the voltage of the battery pack 42 will quickly decrease as the battery cell fails and will then level out at a new voltage V2, and again very gradually decrease until the battery pack nears depletion at which time it will drop quickly. The rapid voltage change and then leveling out of the voltage is characteristic of a depleted cell or a damaged cell in the battery pack 42.

Figure 5:
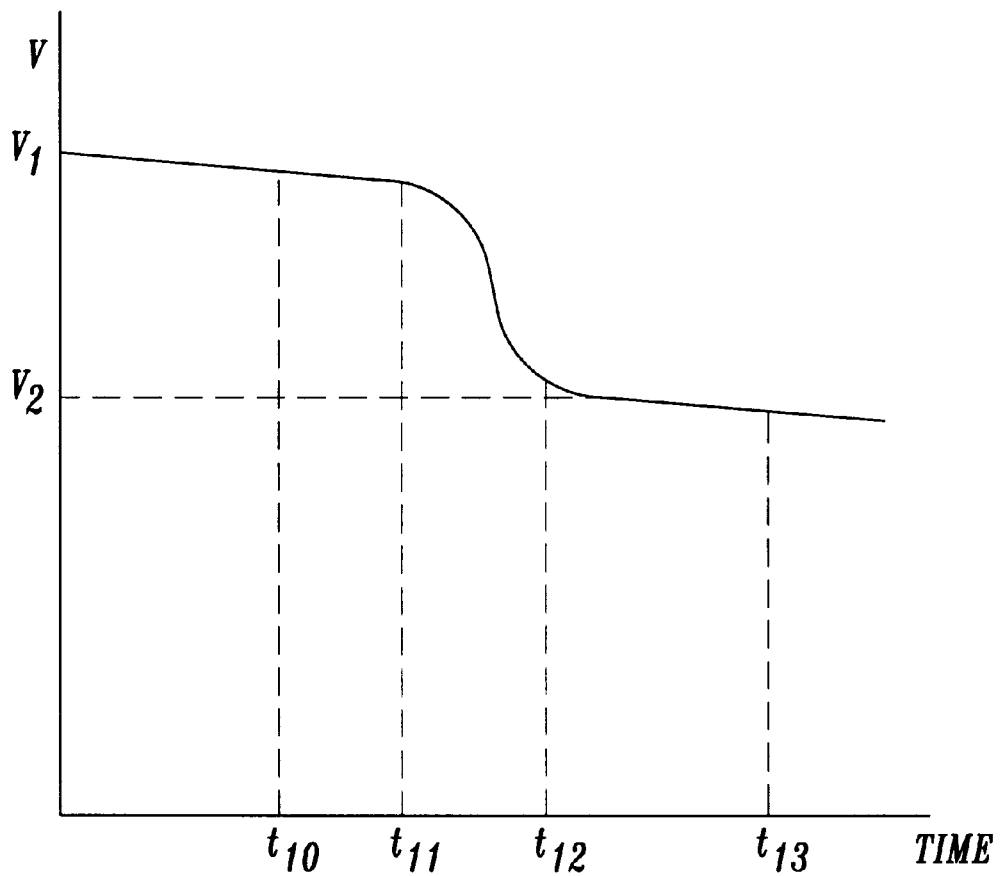
FIG. 5 is a graph depicting the output voltage of the battery pack of FIG. 4 plotted with respect to time.

FIG. 5 illustrates the reversal of a battery cell as a function of voltage of the battery pack 42 plotted against time during discharge of the battery pack. At a time $t_{10}$, the voltage of the battery pack 42 is decreasing gradually while discharging. At a later time $t_{11}$, the voltage of the battery pack 42 decreases at a relatively fast rate as compared to the rate at time $t_{10}$. This sudden change in the rate of voltage drop is characteristic of battery cell depletion and reversal. The reversal of the battery cell lasts until time $t_{12}$, when the voltage of the battery pack 42 returns to a gradual decrease in voltage, as was true at time $t_{10}$ prior to reversal. At time $t_{13}$, the voltage of the battery pack 42 continues to slowly decrease at a rate approximately equal to the rate of voltage change at time $t_{10}$.

The rapid voltage change between times $t_{11}$ and $t_{12}$ is detected by the microprocessor 48. Preferably, the microprocessor 48 is programmed to store a predetermined threshold value prior to reversal. It will be appreciated that the threshold for a particular battery pack prior to reversal depends on the type of battery cells, the initial charge level, the load to be placed on the battery pack, and other factors. During operation, the microprocessor 48 periodically compares the voltage change to the threshold value. If the magnitude of measured voltage change is larger than the threshold value, the microprocessor 48 detects a reversal, indicating the presence of a depleted or damaged battery cell.

It will be appreciated by those skilled in this art and others that high rates of discharge of the battery pack 42 through a battery cell during reversal or continued charging of a battery pack having a bad cell may damage the battery pack, further damage the bad cell, or prevent the battery pack from charging or discharging properly. If a bad battery cell is charged or discharged improperly, damage to the battery cell may be increased to a point which permanently and irreparably compromises the utility of the battery cell or battery pack so that it cannot be recharged or discharged. Accordingly, when the microprocessor 48 detects a reversal caused by battery cell depletion or damage, a warning is preferably provided to a user of the battery pack 42. The warning is provided visually through the display 50 connected to the microprocessor 48 through line 58 and/or audibly through a speaker (not shown). The user may then remove the battery pack 42 and replace the damaged battery cell.

Generally, battery packs contain cells of approximately the same energy storage capacity. Therefore, early depletion of a single battery cell generally means that the battery cell is damaged and has failed to properly take a charge or is failing to discharge correctly. However, in some causes an individual cell may not be damaged but may not have been originally fully charged. Therefore, after detection of a depleted or damaged battery cell, the battery pack may be recharged in an attempt to bring the depleted or damaged cell back to a similar energy storage capacity as the remaining cells in the battery pack. However, if the battery cell is damaged, it will fail to obtain an energy storage capacity that is comparable with the remaining cells in the battery pack. Therefore, during cycling of the battery pack, the damaged cell will again cause a premature voltage change that can be detected and thus provide an indication of the presence of a damaged cell within the battery pack.

The embodiment of the present invention for detecting a damaged battery cell within a battery pack has application in a wide variety of possible environments including external cardiac defibrillators or any other devices including rechargeable battery packs or batteries.

While the preferred embodiment of the invention has been illustrated and described, it will be appreciated that various changes can be made therein without departing from the spirit and scope of the invention. While developed for use in an external cardiac defibrillator, the method and system in accordance with the present invention may also be used in technologies unrelated to defibrillators.

The embodiments of the invention in which an exclusive property or privilege is claimed are defined as follows:

1. A method for monitoring an energy level of a battery pack capable of delivering current to a load, comprising:

providing a battery pack having a monitor cell and at least one other cell, the monitor cell having an initial energy level lower than an initial energy level of the at least one other cell in the battery pack such that through normal use the monitor cell will be depleted before the at least one other cell and thereby provide a measurable indication that the battery pack is nearing depletion while the at least one other cell still has energy remaining;

electrically connecting the monitor cell and the other cells in the battery pack together;

delivering current from the battery pack to the load;

providing a monitoring system for monitoring the voltage on the battery pack for a voltage change that is greater than a predetermined threshold value that is indicative of when the monitor cell is depleted;

detecting a voltage change across the battery pack that is greater than the predetermined threshold value; and providing an indication that the battery pack is nearing depletion upon detection of the voltage change that is greater than the threshold value.

2. The method of claim 1, wherein the monitor cell is rated at less ampere-hours than the at least one other cell in the battery pack.

3. The method of claim 1, wherein the monitor cell is discharged to a predetermined level prior to being connected to the at least one other cell in the battery pack.

4. The method of claim 1, further comprising connecting the battery pack to an external defibrillator and providing an indication to a user of the defibrillator that the battery pack is nearing depletion upon detection of the voltage change greater than the threshold value.

5. The method of claim 4, further comprising providing an indication of an approximate number of shocks that the defibrillator is capable of providing prior to the depletion of the battery pack.

6. The method of claim 1, wherein the monitor cell consists of a plurality of secondary monitor cells, each secondary monitor cell having a predetermined initial energy level and providing a signal indicative of an approximate energy level remaining within the battery pack as each secondary monitor cell is depleted.

7. A system for monitoring an energy level of a battery pack capable of delivering current to a load, the system comprising:

a battery pack having a monitor cell and at least one other cell, the monitor cell having an initial energy level lower than an initial energy level of the at least one other cell in the battery pack such that through normal use the monitor cell will be depleted before the at least one other cell and thereby provide a measurable indication that the battery pack is nearing depletion while the at least one other cell still has energy remaining;

a monitoring system connected to the battery pack to monitor the energy level of the battery pack during discharge of the battery pack, wherein the monitoring system detects a voltage change across the battery pack of at least a predetermined magnitude indicative of when the monitor cell is depleted and provides an indication of an approximate energy level remaining in the battery pack upon depletion of the monitor cell.

8. The system of claim 7, wherein the monitor cell consists of multiple secondary monitor cells, each secondary monitor cell having a different initial energy level, wherein the monitoring system detects the depletion of each secondary monitor cell by detecting a voltage change of at least a predetermined magnitude and providing an indication of a level of energy remaining in the battery pack upon depletion of each secondary monitor cell.

9. The system of claim 7, further comprising a defibrillator, wherein the battery pack is connected to the defibrillator and wherein the monitoring system provides an indication of an approximate operation capacity of the defibrillator when the monitoring system detects the depletion of a monitor cell within the battery pack.

10. The system of claim 7, wherein the monitor cell has a lower ampere-hour storage capacity than at least one of the other cells within the battery pack.

11. The system of claim 7, wherein the monitor cell has an initial energy level lower than the at least one other cell in the battery pack, the initial energy level of the monitor cell having been reduced by predischarging.

12. A defibrillator including:

a battery pack having a monitor cell and at least one other cell, the monitor cell having an initial energy level lower than an initial energy level of the at least one other cell; and a monitoring system for monitoring a voltage across the battery pack, the monitoring system detecting a voltage change across the battery pack that is greater than a predetermined threshold value that is indicative of when the monitor cell is depleted, the monitoring system providing an indication that the battery pack is nearing depletion upon detection of the voltage change that is greater than the threshold value.

13. The defibrillator of claim 12, wherein the monitor cell consists of multiple secondary monitor cells, each secondary monitor cell having a different initial energy level, wherein the monitoring system detects the depletion of each secondary monitor cell by detecting a rate of voltage drop of at least a predetermined magnitude and providing an indication of a level of energy remaining in the battery pack upon depletion of each secondary monitor cell.

14. The defibrillator of claim 12, wherein the monitor cell has a lower ampere-hour storage capacity than at least one of the other cells within the battery pack.

15. The defibrillator of claim 12, wherein the monitor cell has an initial energy level lower than at least one other cell in the battery pack, the initial energy level of the monitor cell having been reduced by predischarging.

16. The defibrillator of claim 12, wherein the monitoring system provides an indication of an approximate operation capacity of the defibrillator upon detection of the depletion of the monitor cell.

* * * * *